US011712172B2

(12) United States Patent
Govari et al.

(10) Patent No.: US 11,712,172 B2
(45) Date of Patent: *Aug. 1, 2023

(54) VISUAL GUIDANCE FOR POSITIONING A DISTAL END OF A MEDICAL PROBE

(71) Applicant: Biosense Webster (Israel) Ltd., Yokneam (IL)

(72) Inventors: Assaf Govari, Haifa (IL); Vadim Gliner, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/896,099

(22) Filed: Jun. 8, 2020

(65) Prior Publication Data
US 2021/0212591 A1    Jul. 15, 2021

Related U.S. Application Data

(60) Provisional application No. 62/875,770, filed on Jul. 18, 2019.

(51) Int. Cl.
*A61B 5/06* (2006.01)
*A61B 5/349* (2021.01)
(Continued)

(52) U.S. Cl.
CPC .............. *A61B 5/066* (2013.01); *A61B 5/287* (2021.01); *A61B 5/343* (2021.01); *A61B 5/349* (2021.01);
(Continued)

(58) Field of Classification Search
CPC ......... A61B 5/066; A61B 5/349; A61B 5/367; A61B 5/343; A61B 5/287; A61B 5/6853; A61B 5/6858
See application file for complete search history.

(56) References Cited

U.S. PATENT DOCUMENTS 5,657,755 A    8/1997 Desai
5,722,402 A    3/1998 Swanson et al.
(Continued)

OTHER PUBLICATIONS

Extended European Search Report dated Oct. 1, 2020, for Application No. 20186466.7, 8 pages.

*Primary Examiner* — Catherine M Voorhees
*Assistant Examiner* — Roland Dinga
(74) *Attorney, Agent, or Firm* — Troutman Pepper Hamilton Sanders LLP (57) ABSTRACT

A method, including receiving, from electrodes positioned within a heart, first signals from at least three of the electrodes indicating electrical activity in tissue with which the at least three of the electrodes engage, and second signals indicating locations of the at least three electrodes. The second signals are processed to compute the locations of the at least three electrodes and to determine a geometric center of the locations. Based on the signals, an electroanatomical map is generated for an area of the tissue including the geometric center, and an arrhythmia focus is determined in the map. A circle is presented, and within the circle, a region of the map is presented including the geometric center and the focus so that the geometric center on the map aligns with a center of the circle, the region within the circle indicating a spatial relationship between the geometric center and the focus.

23 Claims, 6 Drawing Sheets

(51) Int. Cl.
 *A61B 5/367* (2021.01)
 *A61B 5/343* (2021.01)
 *A61B 5/287* (2021.01)
 *A61B 5/00* (2006.01)

(52) U.S. Cl.
 CPC ............ *A61B 5/367* (2021.01); *A61B 5/6853* (2013.01); *A61B 5/6858* (2013.01)

(56) References Cited

U.S. PATENT DOCUMENTS

| | | |
|---|---|---|
| 5,944,022 A | 8/1999 | Nardella et al. |
| 5,983,126 A | 11/1999 | Wittkampf |
| 6,456,864 B1 | 9/2002 | Swanson et al. |
| 8,224,432 B2 | 7/2012 | MacAdam et al. |
| 8,326,419 B2 | 12/2012 | Rosenberg et al. |
| 8,577,450 B1 * | 11/2013 | Chmiel .................. A61B 5/339 600/523 |
| 2003/0013958 A1 | 1/2003 | Govari et al. |
| 2008/0188765 A1 * | 8/2008 | Stolarski .................. A61B 5/35 600/518 |
| 2013/0184569 A1 | 7/2013 | Strommer et al. |
| 2013/0274582 A1 | 10/2013 | Afonso et al. |
| 2014/0303452 A1 * | 10/2014 | Ghaffari ................. A61B 18/14 601/3 |
| 2016/0007852 A1 | 1/2016 | Warner et al. |
| 2018/0296108 A1 * | 10/2018 | Stewart .................. A61B 34/25 |
| 2018/0325418 A1 | 11/2018 | Ghoraani et al. |
| 2020/0375489 A1 * | 12/2020 | Govari ................. A61B 5/6859 |

\* cited by examiner

VISUAL GUIDANCE FOR POSITIONING A DISTAL END OF A MEDICAL PROBE

CROSS-REFERENCE TO RELATED APPLICATIONS

This application claims the benefit of U.S. Provisional Patent Application 62/875,770, filed Jul. 18, 2019, which is incorporated herein by reference.

FIELD OF THE INVENTION

The present invention relates generally to medical imaging, and specifically to providing visual feedback to aid in guiding a distal end of a medical probe to a location in a body cavity requiring medical treatment.

BACKGROUND OF THE INVENTION

Some medical procedures, such as mapping a cavity of a body organ (e.g., a heart), are performed by inserting a medical probe into the cavity. In some configurations, the medical probe comprises a distal segment that comprises multiple electrodes that can measure a physiological property such as a local surface electrical potential at a location in a heart.

Examples of medical probes comprising multiple electrodes include balloon catheters and basket catheters. In some configurations, these medical probes can deliver radio frequency (RF) current to ablate tissue in contact with the probe's distal end in order to provide a therapeutic result.

U.S. Pat. No. 8,577,450 to Chmiel et al. describes a graphic interface for multi-spine probe. The graphic interface includes a circle, the center of the circle representing a location of the distal end of the body of a catheter, and radii of the circle representing locations orientations of spines mounted at the distal end of the catheter.

U.S. Patent Application 2013/0274582 to Afonso et al. describes a method for diagnosing arrhythmias and directing catheter therapies. The method includes creating, for a catheter having a spiral-shaped distal comprising multiple electrodes, a representation of the catheter that may be superimposed on a map, model or image of the tissue.

U.S. Pat. No. 5,722,402 to Swanson et al. describes a method for guiding movable electrode elements within multiple-electrode structures. The method includes presenting, using different shades of color, a normalized distribution of voltages detected by electrodes of a basket catheter.

U.S. Patent Application 2013/0184569 to Strommer et al. describes a method for producing an electrophysiological map of a heart. The method includes generating a local activation time map of a heart by superimposing a representation of the position of a distal tip of a catheter on a marked image.

U.S. Pat. No. 8,224,432 to MacAdam et al. describes a method of rapid 3D mapping using multi-electrode position data. The method includes applying color coding to a map which depicts variations in activation time or any other parameter being mapped in accordance with a color scale.

U.S. Pat. No. 8,326,419 to Rosenberg et al. describes a method for therapy optimization via multi-dimensional mapping. The method includes generating an electromechanical delay map by subtracting local electrical activation times from corresponding local mechanical activation times, and rendering at least the electromechanical delay map to a display. The method may also include rendering an electromechanical delay map in color, where a color scale quantitatively identifies electromechanical delay values (e.g., via open or filled contours).

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method, including receiving, from an intracardiac catheter, having a distal end including a plurality of electrodes, within a heart of a subject, first signals from at least three of the electrodes responsive to electrical activity in myocardial tissue with which the at least three of the electrodes are in contact, receiving second signals that are indicative of respective location coordinates of the at least three electrodes within the heart, processing the second signals so as to compute the respective location coordinates of the at least three electrodes and to determine a geometric center of the respective location coordinates, generating, based on the first signals and the second signals, an electroanatomical map for an area of the myocardial tissue including the determined geometric center, determining, in the map, a focus of an arrhythmia in the area of the myocardial tissue, presenting, on a display, a circle, and presenting, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

In some embodiments, the electrical activity includes local activation time values. In additional embodiments, presenting the region of the map with the focus of the arrhythmia includes plotting the local activation time values against their respective locations.

In one embodiment, the arrhythmia includes a rotor having at least one focus. In another embodiment, the arrhythmia includes a focal.

In further embodiments, presenting the region of the map with the geometric center includes presenting, in the circle, an icon at a position corresponding to a location of the focus of the arrhythmia relative to the geometric center. In other embodiments, presenting the circle and the region of the map includes overlaying the circle on the electroanatomical map. In supplemental embodiments, the method also includes presenting, within the circle, a path of the arrhythmia from the focus of the arrhythmia.

In one embodiment, the intracardiac catheter includes a balloon catheter. In another embodiment, the intracardiac catheter includes a basket catheter.

In an additional embodiment, generating the electroanatomical map may include presenting the map on the display at a first resolution. In this additional embodiment, presenting the region may include presenting the region at a second resolution greater than the first resolution.

There is also provided, in accordance with an embodiment of the present invention an apparatus, including an intracardiac catheter configured to be inserted into a cardiac chamber, a plurality of electrodes affixed to a distal end of the intracardiac catheter, a display, and a processor configured to receive, from the intracardiac catheter inserted into a given cardiac chamber, first signals from at least three of the electrodes responsive to electrical activity in myocardial tissue with which the at least three of the electrodes are in contact, to receive second signals that are indicative of respective location coordinates of the at least three electrodes within the heart, to process the second signals so as to compute the respective location coordinates of the at least three electrodes and to determine a geometric center of the respective location coordinates, to generating, based on the first signals and the second signals, an electroanatomical map for an area of the myocardial tissue including the determined geometric center, to determine, in the map, a focus of an arrhythmia in the area of the myocardial tissue, to present, on the display, a circle; and to present, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

There is further provided, in accordance with an embodiment of the present invention a computer software product, operated in conjunction with a intracardiac catheter having a distal end including a plurality of electrodes, the product including a non-transitory computer-readable medium, in which program instructions are stored, which instructions, when read by a computer, cause the computer to receive, from the intracardiac catheter positioned within a heart of a subject, first signals from at least three of the electrodes responsive to electrical activity in myocardial tissue with which the at least three of the electrodes are in contact, to receive second signals that are indicative of respective location coordinates of the at least three electrodes within the heart, to process the second signals so as to compute the respective location coordinates of the at least three electrodes and to determine a geometric center of the respective location coordinates, to generate, based on the first signals and the second signals, an electroanatomical map for an area of the myocardial tissue including the determined geometric center, to determine, in the map, a focus of an arrhythmia in the area of the myocardial tissue, to present, on a display, a circle, and to present, within the circle, a region of the map including the geometric center and the focus of the arrhythmia so that the geometric center on the map aligns with a center of the circle, wherein the region of the map presented within the circle indicates a spatial relationship between the geometric center and the focus of the arrhythmia.

BRIEF DESCRIPTION OF THE DRAWINGS

The disclosure is herein described, by way of example only, with reference to the accompanying drawings, wherein.

DETAILED DESCRIPTION OF EMBODIMENTS

When using a medical probe having multiple electrodes (e.g., basket catheter or a balloon catheter), it may be difficult to accurately position the electrodes with respect to a desired location. For example, during a medical procedure, a medical professional may want to position particular electrodes of a catheter on or close to a focal source of an arrhythmia in myocardial tissue. However, there may be instances during the procedure when the electrodes and/or portions of the tissue are not directly visible to the medical professional. In these instances, even if the electrode locations can be determined, and a camera can be used to view the tissue, it can still be challenging for the medical professional to accurately position the electrodes at the desired locations.

Embodiments of the invention present methods and systems for guiding a distal end of a medical probe toward a treatment location. As described hereinbelow, first and second signals are received from an intracardiac catheter positioned within a heart of a subject and having a distal end comprising a plurality of electrodes. In embodiments of the present invention, the first signals are received from at least three of the electrodes responsive to electrical activity in myocardial tissue with which the at least three of the electrodes are in contact, and the second signals are indicative of respective location coordinates of the at least three electrodes within the heart.

The second signals are processed so as to compute the respective location coordinates of the at least three electrodes, and to determine a geometric center of the respective location coordinates. Based on the first signals and the second signals, an electroanatomical map is generated for an area of the myocardial tissue comprising the determined geometric center, and a focus of an arrhythmia in the area of the myocardial tissue is determined in the map.

To provide positioning guidance to a medical professional, a circle is presented on a display, and within the circle, a region of the map comprising the geometric center and the focus of the arrhythmia is presented so that the geometric center (of the location coordinates of the electrodes) on the map aligns with a center of the circle. In embodiments of the present invention, the region of the map presented within the circle indicates a spatial relationship between the geometric center and the focus of the arrhythmia.

In some embodiments, systems implementing embodiments of the present invention can present the spatial relationship as a circular bulls-eye, where the bulls-eye indicates the location of the focus of the arrhythmia relative to the electrodes. The location of the bulls-eye in the circle can be used to verify that electrodes are close to, or are contacting a desired region. If the electrodes are close to (but not in contact with) the desired region, the medical professional can use the image (e.g., the bulls-eye) as a visual guide for repositioning the distal end of the medical probe in order to move the electrodes to the desired locations.

SYSTEM DESCRIPTION

Figure 1:
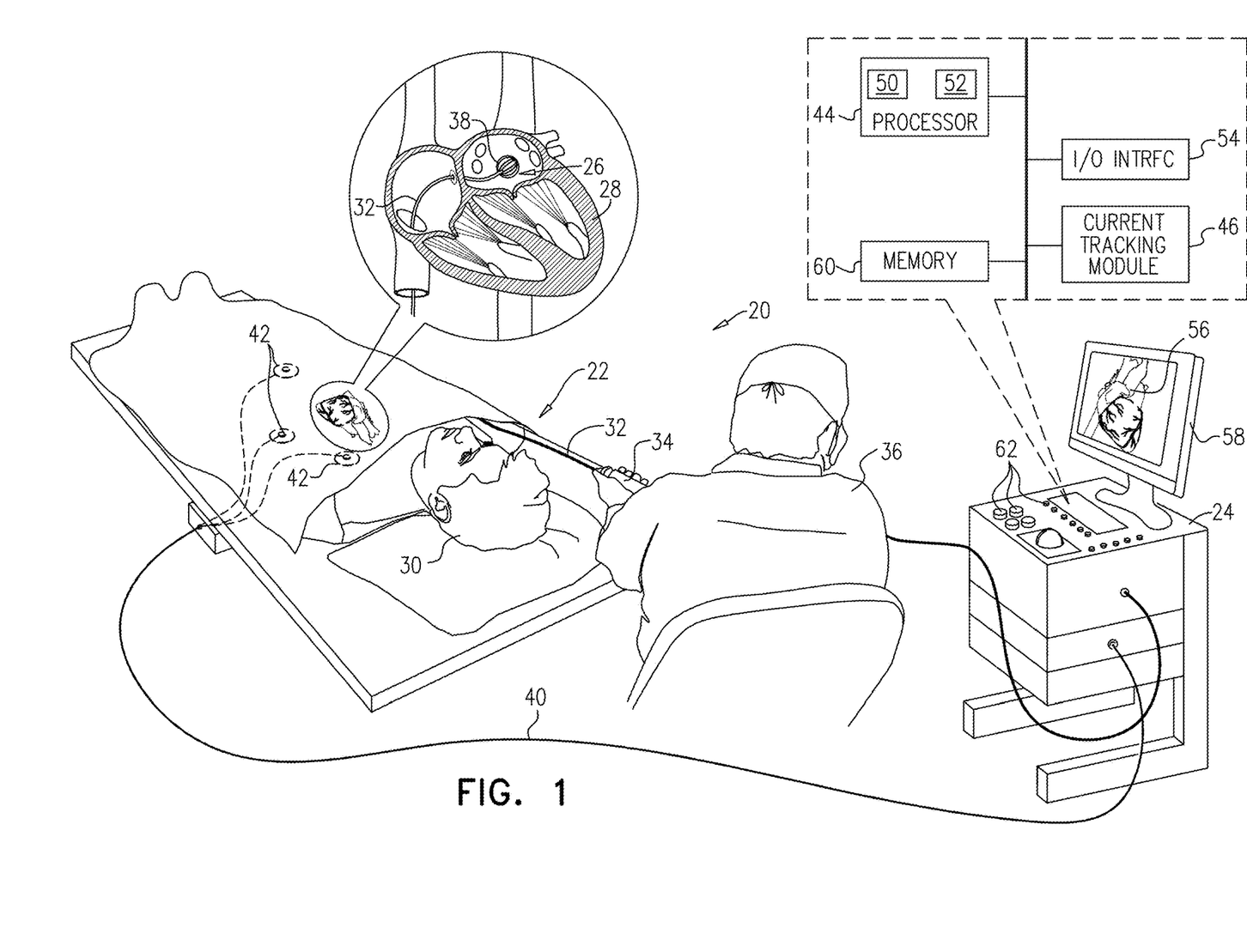
FIG. 1 is a schematic, pictorial illustration of a medical system comprising a basket catheter with a distal end, in accordance with an embodiment of the present invention.
Figure 2:
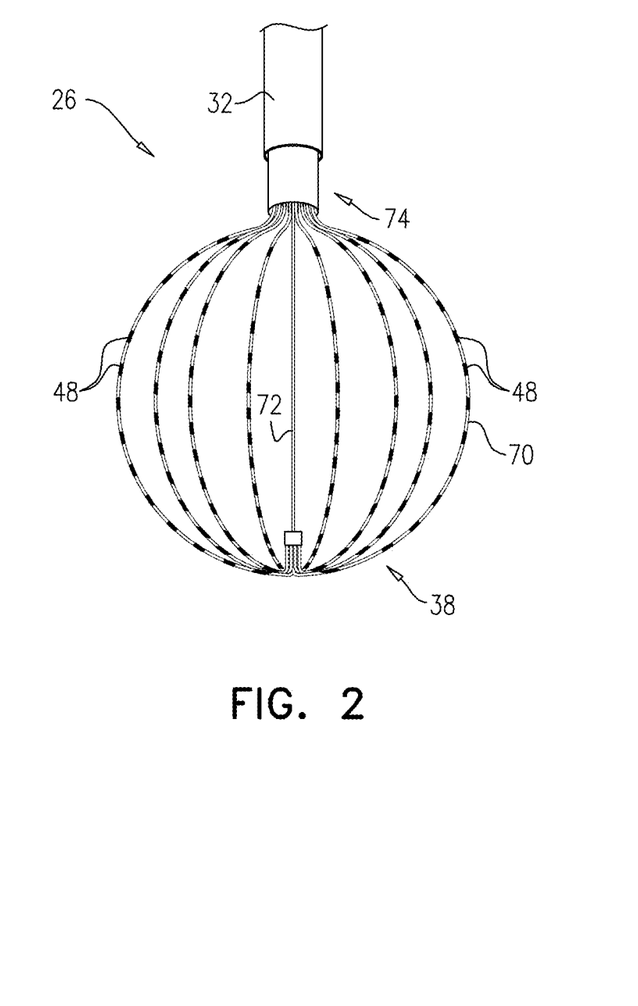
FIG. 2 is a schematic pictorial illustration of the distal end of the basket catheter comprising electrodes affixed to splines of the catheter, in accordance with an embodiment of the present invention.

FIG. 1 is a schematic, pictorial illustration of a medical system 20 comprising medical probe 22 and a control console 24, and FIG. 2 is a schematic pictorial illustration of a distal end 26 of the medical probe, in accordance with an embodiment of the present invention. Medical system 20 may be based, for example, on the CARTO® system, produced by Biosense Webster Inc. of 33 Technology Drive, Irvine, Calif. 92618 USA. In embodiments described hereinbelow, medical probe 22 can be used for diagnostic or therapeutic treatment, such as for mapping electrical potentials in a heart 28 of a patient 30 (also referred to herein as a subject). Alternatively, medical probe 22 may be used, mutatis mutandis, for other therapeutic and/or diagnostic purposes in the heart or in other body organs.

Probe 22 comprises an insertion tube 32 and a handle 34 coupled to a proximal end of the insertion tube. During a medical procedure, a medical professional 36 can insert probe 22 through the vascular system of patient 30 so that distal end 26 of the medical probe enters a chamber of heart 28. Upon distal end 26 entering the chamber of heart 28, medical professional 36 can deploy an electrode assembly 38 affixed to distal end 26, and the medical professional can manipulate handle 34 to position splines of the electrode assembly so that electrodes on the splines engage myocardial tissue at a desired location or locations. In embodiments of the present invention, electrode assembly 38 may comprise a basket-shaped electrode assembly (as described in the description referencing FIG. 2 hereinbelow) affixed to a basket catheter or a balloon electrode assembly affixed to a balloon catheter.

In the configuration shown in FIG. 1, control console 24 is connected, by a cable 40, to body surface electrodes, which typically comprise adhesive skin patches 42 that are affixed to patient 30. Control console 24 comprises a processor 44 that, in conjunction with a current tracking module 46, determines location coordinates of distal end 26 inside heart 28 based on impedances and/or currents measured between adhesive skin patches 42 and electrodes 48 (FIG. 2) that are affixed to splines of electrode assembly 38. In addition to being used as location sensors during a medical procedure, electrodes 48 may perform other tasks such as measuring electrical activity of heart 28.

As described hereinabove, in conjunction with current tracking module 46, processor 44 may determine location coordinates of distal end 26 inside heart 28 based on impedances and/or currents measured between adhesive skin patches 42 and electrodes 48. Such a determination is typically after a calibration process relating the impedances or currents to known locations of the distal end has been performed. In embodiments of the present invention, electrodes 48 can also be configured to apply a signal to tissue in heart 28, and/or to measure a certain physiological property (e.g., the local surface electrical potential) at a location in the heart.

Processor 44 may comprise real-time noise reduction circuitry 50 typically configured as a field programmable gate array (FPGA), followed by an analog-to-digital (A/D) signal conversion integrated circuit 52. The processor can pass the signal from A/D circuit 52 to another processor and/or can be programmed to determine the location coordinates referred to above.

Although the medical system shown in FIG. 1 uses impedance or current-based sensing to measure a location of distal end 26, other location tracking techniques may be used (e.g., techniques using magnetic-based sensors). Impedance and current-based location tracking techniques are described, for example, in U.S. Pat. Nos. 5,983,126, 6,456,864 and 5,944,022. The methods of location sensing described hereinabove are implemented in the above-mentioned CARTO® system and are described in detail in the patents cited above.

Control console 24 also comprises an input/output (I/O) communications interface 54 that enables the control console to transfer signals from, and/or transfer signals to electrodes 48 and adhesive skin patches 42. Based on signals received from electrodes 48 and/or adhesive skin patches 42, processor 44 can generate an electroanatomical map 56 that shows the location of distal end 26 in the patient's body. During the procedure, processor 44 can present map 56 to medical professional 36 on a display 58, and store data representing the electroanatomical map in a memory 60. Memory 60 may comprise any suitable volatile and/or non-volatile memory, such as random access memory or a hard disk drive. In some embodiments, medical professional 36 can manipulate map 56 using one or more input devices 62. In alternative embodiments, display 58 may comprise a touchscreen that can be configured to accept inputs from medical professional 36, in addition to presenting map 56.

In the example shown in FIG. 2, electrode assembly 38 is configured as a basket-shaped electrode assembly that has a plurality of splines 70 connected at their proximal and distal ends. Basket-shaped electrode assembly 38 has an expanded arrangement wherein splines 70 bow radially outwardly and a collapsed arrangement wherein the splines are arranged generally along the axis of insertion tube 32. In some embodiments, the distance between the proximal and distal ends of basket-shaped electrode assembly 38 may be shortened, such as by moving puller wire 72 proximally, causing splines 70 to bow outwards into the expanded configuration. During a medical procedure, basket-shaped electrode assembly 38 can assume an expanded configuration when unconstrained, such as by being advanced out of a lumen 74 at distal end 26.

Each given spline 70 comprises one or more electrodes 48. In addition to using electrodes 48 to determine the location of basket-shaped electrode assembly 38, the electrodes can also be used to measure a physiological property such as local surface electrical potentials at respective locations on myocardial tissue 110. In additional embodiments, electrodes 48 can be configured to deliver ablation power (e.g., radio-frequency energy) to the myocardial tissue.

Figure 3:
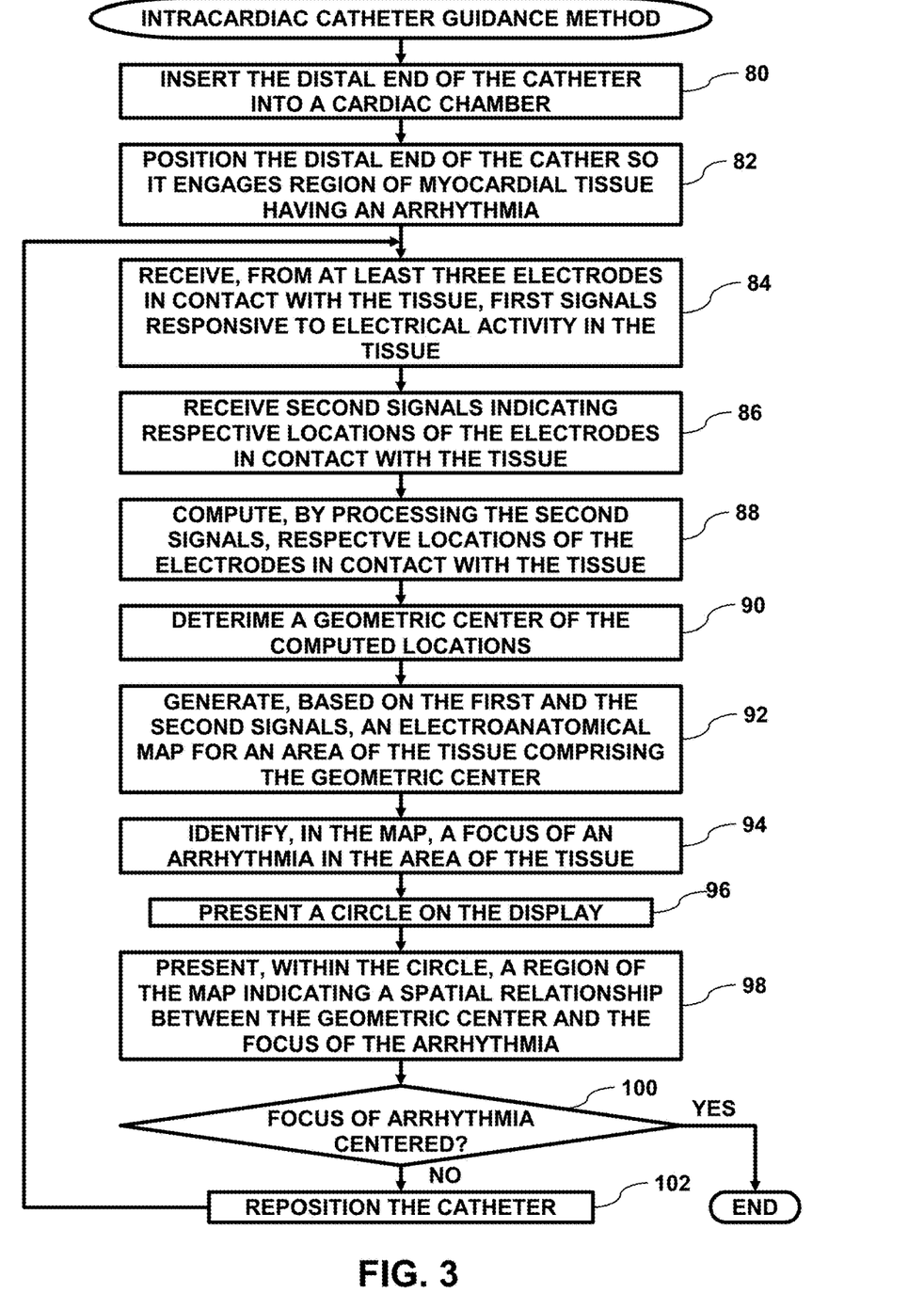
FIG. 3 is a flow diagram that schematically illustrates a method of providing, to medical professional, visual feedback for guiding the distal end of the balloon catheter, in accordance with an embodiment of the present invention.
Figure 4:
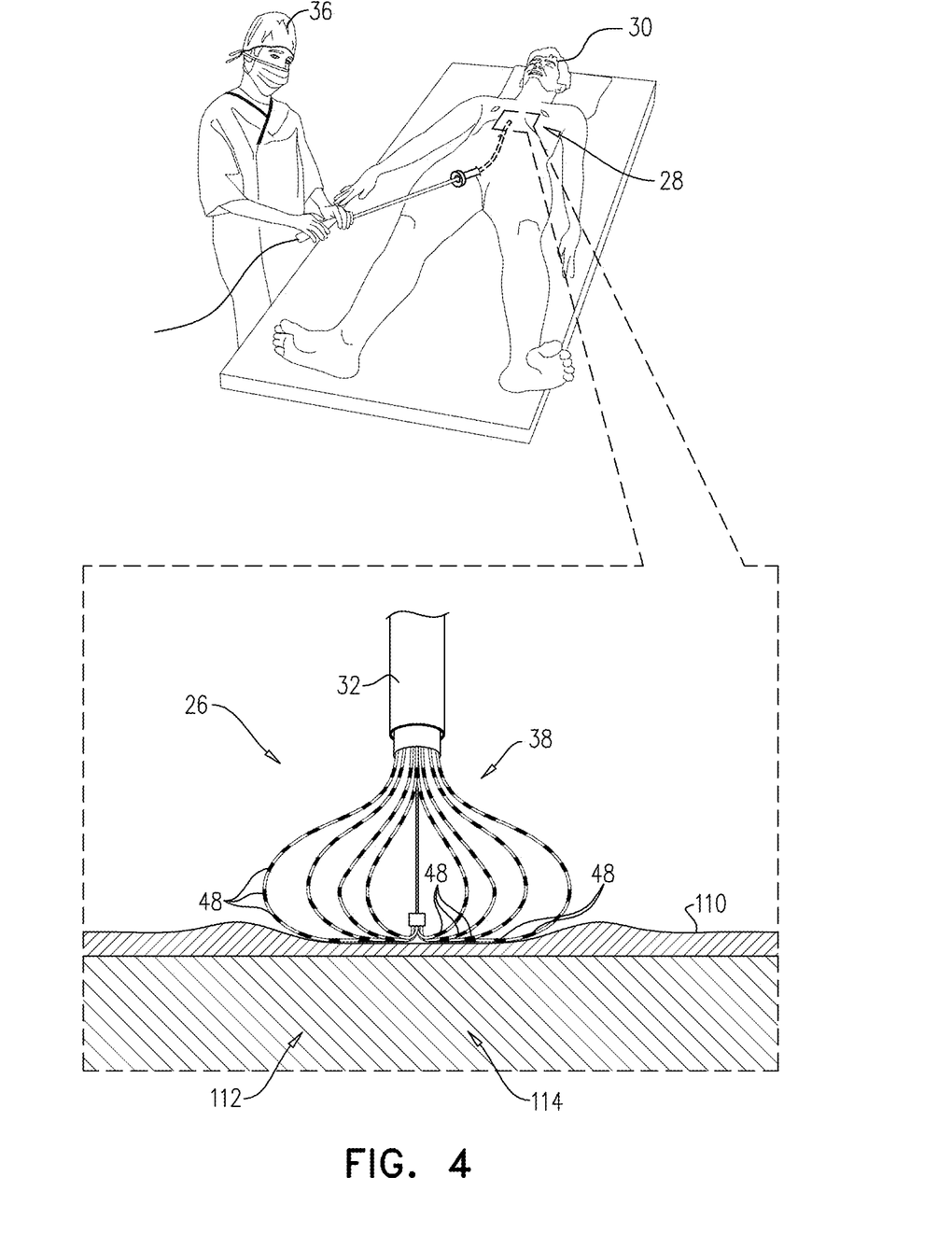
FIG. 4 is a schematic pictorial illustration of the electrodes engaging myocardial tissue in a heart during a medical procedure, in accordance with an embodiment of the present invention.

FIG. 3 is a flow diagram that schematically illustrates a method of providing, to medical professional 36, visual feedback for guiding balloon 38 in heart 28, and FIG. 4 is a schematic pictorial illustration of electrodes 48 engaging myocardial tissue 110 in the heart during a medical procedure, in accordance with an embodiment of the present invention. While the steps of the flow diagram are described using medical probe 22 comprising electrodes 48 mounted on basket-shaped electrode assembly 38, using any other type of medical probe, e.g., a balloon catheter, that comprises multiple electrodes that can simultaneously measure physiological properties at respective locations on myocardial tissue 110 are considered to be within the spirit and scope of the present invention.

In an insertion step 80, medical professional 36 inserts distal end 26 of medical probe 22 into a chamber of heart 28. Upon inserting distal end 26 into the chamber, medical professional 36 can deploy balloon 38 from lumen 72, and inflate the balloon using embodiments described hereinabove.

In a positioning step 82, medical professional 36 manipulates handle 34 so that electrodes 48 at distal end 26 engages a region 112 on myocardial tissue 110 having an arrhythmia.

In a first receive step 84, processor 44 receives, from at least three electrodes 48, first signals responsive to electrical activity in the myocardial tissue engaged by the electrodes. In some embodiments, the electrical activity indicates local activation times in the myocardial tissue.

In a second receive step 86, the processor receives second signals indicating respective locations of the electrodes engaging the myocardial tissue. In the configuration shown in FIG. 1, processor 44 receives the second signals from the body surface electrodes in adhesive skin patches 42 in response to electrical currents conveyed by the processor to electrodes 48.

In a computation step 88, processor 44 processes the received second signals to compute respective locations of the electrodes engaging myocardial tissue 110, and in a determination step 90, the processor determines, on the myocardial tissue, a geometric center 114 of the computed locations.

In a generation step 92, processor 44 generates, for region 112, electroanatomical map 56 based on the received first and second signals, and in an identification step 94, the processor identifies, in the electroanatomical map, a focus of an arrhythmia. Arrythmias may be identified using local activation times (LATs) of the myocardial tissue, and the processor may identify the focus of a particular arrythmia using LATs of the tissue. For example, the processor may identify the focus of a focal arrythmia as being a region of the arrythmic tissue having the lowest LAT; and may identify the focus of a rotor as being the region of the arrythmic tissue about which the LAT values rotate. Implementation of the present embodiment using other methods for processor 44 to identify the focus of an arrythmia are also considered to be comprised within the scope of the present invention.

In a first presentation step 96, processor 44 presents a circle on display 58, and in a second presentation step 98, the processor presents, within the circle, a region of the electroanatomical map comprising the geometric center and the focus of the arrhythmia so that the geometric center on the electroanatomical map aligns with a center of the circle.

As presented in FIGS. 5-9 which are described hereinbelow, the region of the electroanatomical map presented within the circle indicates a spatial relationship between the geometric center and the focus of the arrhythmia. In some embodiments, processor 44 can present the spatial relationship by plotting local activation time values against their respective locations.

Figure 5:
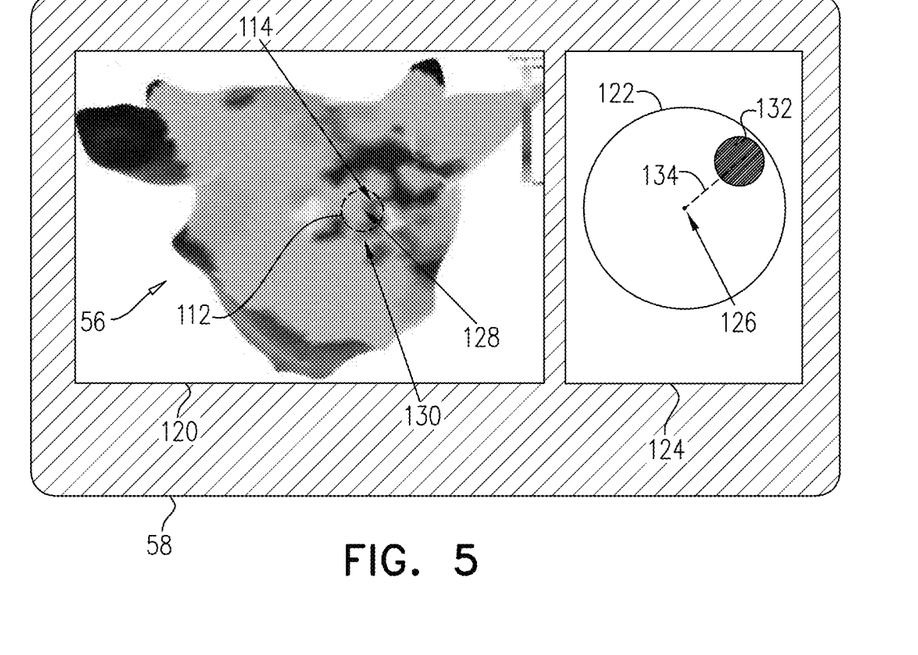
FIG. 5 is a schematic pictorial illustration of presenting an electroanatomical map on a display, in accordance with a first embodiment of the present invention.

FIG. 5 is a schematic pictorial illustration of electroanatomical map 56 presented on display 58, in accordance with a first embodiment of the present invention. In the first embodiment of the present invention, processor 44 presents, on display 58, electroanatomical map 56 in a first window 120, and a circle 122 in a second window 124. Circle 122 corresponds to a region of electroanatomical map 56 so that a center 126 of circle 122 aligns with a geometric center 128 of an arrhythmia 130. In some embodiments, processor 44 can present a visual indicator 132 (e.g., an icon) that corresponds to a location of a focus 136 of arrhythmia and indicates a spatial relationship between geometric center 128 and the focus of the arrhythmia. In embodiments of the present invention, processor 44 can present the spatial relationship as a "bulls-eye" that indicates a distance 134 between visual indicator 132 (that corresponds to focus 136) and circle center 126 (that corresponds to geometric center 128).

In embodiments of the present invention, processor 44 can present map 56 at a first resolution, and present circle 122 comprising the region on the myocardial tissue having the arrhythmia at a second resolution greater than the first resolution. Presenting the region on the myocardial tissue having the arrhythmia at a higher resolution (and therefore presenting the region having the arrhythmia in more detail) can assist medical professional 36 in positioning electrodes 48 at appropriate locations for treating arrhythmia 130.

Figure 6:
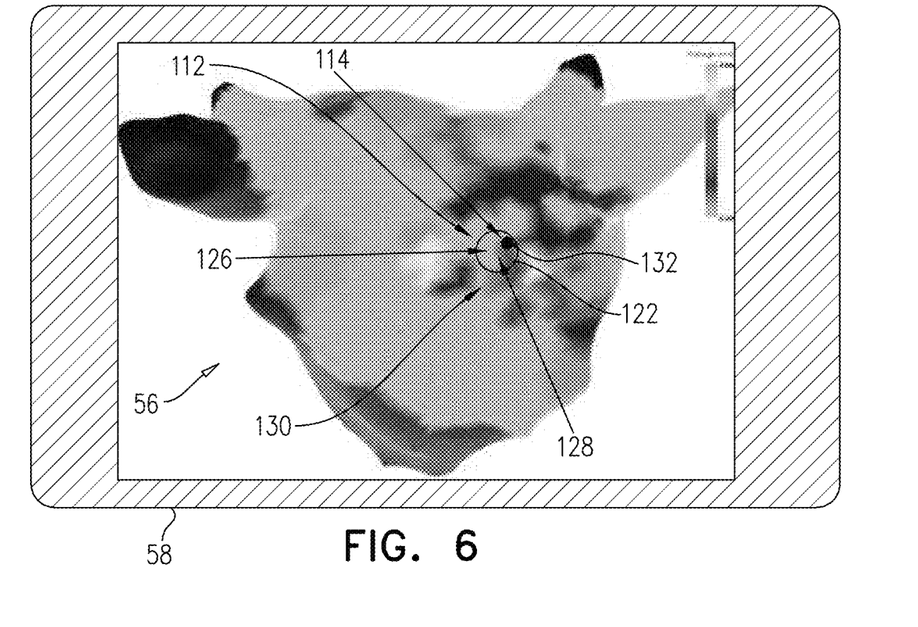
FIG. 6 is a schematic pictorial illustration of presenting the electroanatomical map on the display, in accordance with a second embodiment of the present invention.

FIG. 6 is a schematic pictorial illustration of electroanatomical map 56 presented on display 58, in accordance with a second embodiment of the present invention. In the second embodiment of the present invention, processor 44 presents, on display 58, electroanatomical map 56, and overlays circle 122 and visual indicator 132 on the electroanatomical map 56 so that circle center 126 aligns with geometric center 128 and visual indicator 132 aligns with arrhythmia focus 136.

In a third embodiment, processor 44 can combine the first and second embodiments described supra by presenting circle 122 and visual indicator 132 in window 124, presenting electroanatomical map 56 in window 120, and overlaying the circle and the visual indicator on the electroanatomical map.

In the examples presented in FIG. 5 (and in FIGS. 6-9), geometric center 128 is in close proximity to focus 136, and processor 44 presents visual indicator 132 within circle 122. However, if geometric center 128 is not in close proximity to focus 136, processor 44 can presents visual indicator 132 outside circle 122.

Returning to the flow diagram, in a decision step 100, if medical professional 36 observes that the focus of the ablation is not centered in the circle (e.g., as shown in FIGS. 5, 6, 7A, 8A and 9A), then the medical professional repositions distal end 26 in a repositioning step 102, and the method continues with step 84. If medical professional 36 observes that the focus of the ablation is centered in the circle (e.g., as shown in FIGS. 7B, 8B and 9B), then the method ends. In some instances, medical professional can instruct control console 24 to deliver ablation power (e.g., radio-frequency energy) to electrodes 48 in order to ablate the region of myocardial tissue comprising the arrhythmia.

Figure 7A:
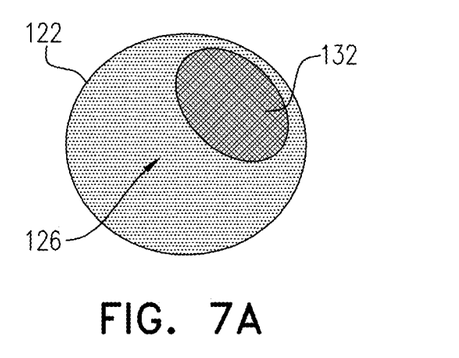
FIGS. 7A and 7B are schematic pictorial illustrations of visual indicators that can be presented on the display to help a medical professional position the distal end of the medical probe at an area of tissue requiring treatment, in accordance with embodiments of the present invention.
Figure 7B:
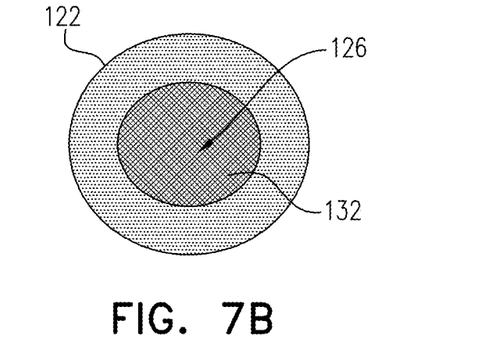

FIGS. 7A and 7B, also referred to herein collectively as FIG. 7, are schematic pictorial illustrations of circle 122 and visual indicator 132 for arrhythmia 130 comprising a focal arrhythmia, in accordance with an embodiment of the present invention. In FIG. 7A, visual indicator 132 is not aligned with circle center 126, thereby indicating that geometric center 128 is not aligned with focus 136. In FIG. 7B, visual indicator 132 is aligned with (i.e., overlaps) circle center 126, thereby indicating that geometric center 128 is aligned with focus 136.

Figure 8A:
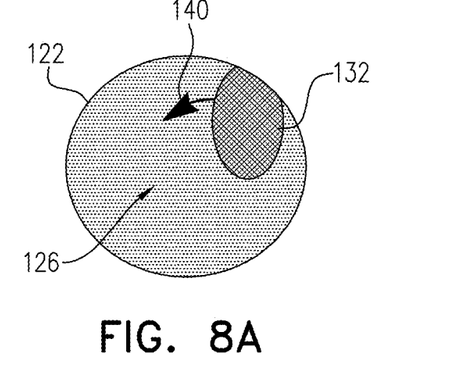
FIGS. 8A and 8B are schematic pictorial illustrations of circle and visual indicator for arrhythmia comprising a rotor arrhythmia having a single focus.
Figure 8B:
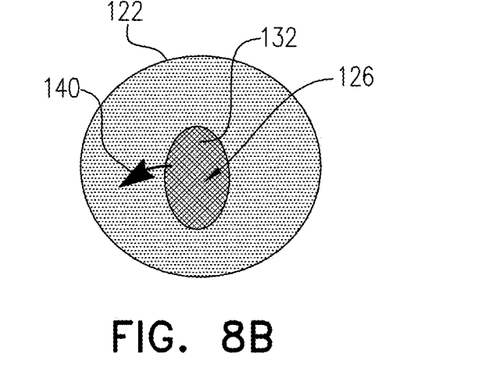

FIGS. 8A and 8B, also referred to herein collectively as FIG. 8, are schematic pictorial illustrations of circle 122 and visual indicator 132 for arrhythmia 130 comprising a rotor arrhythmia having a single focus 136, in accordance with an embodiment of the present invention. In the example presented in FIGS. 8A and 8B, an arrow 140 indicates a path of the arrhythmia from focus 136 in myocardial tissue 110. In FIG. 8A, visual indicator 132 is not aligned with circle center 126, thereby indicating that geometric center 128 is not aligned with focus 136. In FIG. 8B, visual indicator 132 is aligned with (i.e., overlaps) circle center 126, thereby indicating that geometric center 128 is aligned with focus 136.

Figure 9A:
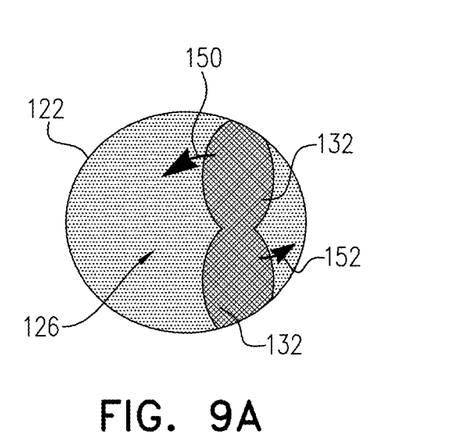
FIGS. 9A and 9B are schematic pictorial illustrations of circle and visual indicator for arrhythmia comprising a rotor arrhythmia having two focuses.
Figure 9B:
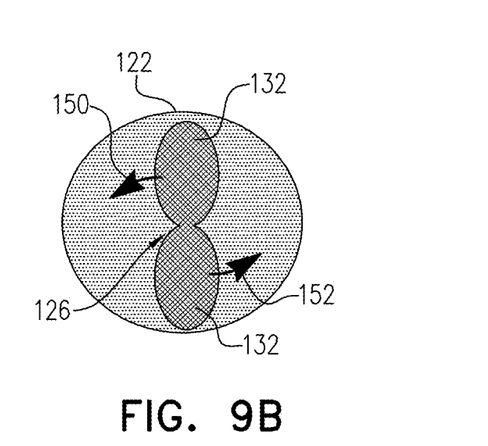

FIGS. 9A and 9B, also referred to herein collectively as FIG. 9, are schematic pictorial illustrations of circle 122 and visual indicator 132 for arrhythmia 130 comprising a rotor arrhythmia having two focuses 136, in accordance with an embodiment of the present invention. In the example presented in FIGS. 9A and 9B, arrows 150 and 152 indicate paths of the arrhythmias from their respective focuses 136 in myocardial tissue 110. In FIG. 9A, visual indicator 132 is not aligned with circle center 126, thereby indicating that geometric center 128 is not aligned with focus 136. In FIG. 9B, visual indicator 132 is aligned with (i.e., overlaps) circle center 126, thereby indicating that geometric center 128 is aligned with focus 136.

While the description referencing FIGS. 5, 6, 7A, 7B, 8A, 8B and 9A and 9B describe processor 44 presenting circle 122 on display 58, presenting any type of ovular shape corresponding to a region of map 56 is considered to be within the spirit and scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
   (a) receiving, from an intracardiac catheter, having a distal end comprising a plurality of electrodes, within a heart of a subject, first signals from at least three of the electrodes responsive to electrical activity in myocardial tissue with which the at least three of the electrodes are in contact;
   (b) receiving, from at least one of the intracardiac catheter or at least one body surface electrode applied to a body surface of the subject, second signals that are indicative of respective location coordinates of the at least three electrodes within the heart;
   (c) processing the second signals so as to compute the respective location coordinates of the at least three electrodes and to determine a geometric center of the respective location coordinates;
   (d) generating, based on the first signals and the second signals, an electroanatomical map for an area of the myocardial tissue comprising the determined geometric center;
   (e) determining, in the map, a focus of an arrhythmia in the area of the myocardial tissue;
   (f) presenting, on a display, a circle; and
   (g) presenting, within the circle, a region of the map comprising the geometric center and the focus of the arrhythmia so that the geometric center on the map aligns with a center of the circle, the region of the map presented within the circle indicating a spatial relationship between the geometric center and the focus of the arrhythmia.

2. The method according to claim 1, the electrical activity comprising local activation time values.

3. The method according to claim 2, presenting the region of the map comprising the focus of the arrhythmia comprising plotting the local activation time values against their respective locations.

4. The method according to claim 1, the arrhythmia comprising a rotor having at least one focus.

5. The method according to claim 1, the arrhythmia comprising a focal.

6. The method according to claim 1, presenting the region of the map comprising the geometric center comprising presenting, in the circle, an icon at a position corresponding to a location of the focus of the arrhythmia relative to the geometric center.

7. The method according to claim 1, presenting the circle and the region of the map comprising overlaying the circle on the electroanatomical map.

8. The method according to claim 1, and comprising presenting, within the circle, a path of the arrhythmia from the focus of the arrhythmia.

9. The method according to claim 1, the intracardiac catheter comprising a balloon catheter.

10. The method according to claim 1, the intracardiac catheter comprising a basket catheter.

11. The method according to claim 1, generating the electroanatomical map comprising presenting the map on the display at a first resolution, and presenting the region comprising presenting the region at a second resolution greater than the first resolution.

12. An apparatus, comprising:
   (a) an intracardiac catheter configured to be inserted into a cardiac chamber;
   (b) a plurality of electrodes affixed to a distal end of the intracardiac catheter;
   (c) a display; and
   (d) a processor configured:
      (i) to receive, from the intracardiac catheter inserted into a given cardiac chamber, first signals from at least three of the electrodes responsive to electrical activity in myocardial tissue with which the at least three of the electrodes are in contact,
      (ii) to receive, from at least one of the intracardiac catheter or at least one body surface electrode applied to a given body surface, second signals that are indicative of respective location coordinates of the at least three electrodes within the heart,
      (iii) to process the second signals so as to compute the respective location coordinates of the at least three electrodes and to determine a geometric center of the respective location coordinates,
      (iv) to generate, based on the first signals and the second signals, an electroanatomical map for an area of the myocardial tissue comprising the determined geometric center,
      (v) to determine, in the map, a focus of an arrhythmia in the area of the myocardial tissue,
      (vi) to present, on the display, a circle, and
      (vii) to present, within the circle, a region of the map comprising the geometric center and the focus of the arrhythmia so that the geometric center on the map aligns with a center of the circle, the region of the map presented within the circle indicating a spatial relationship between the geometric center and the focus of the arrhythmia.

13. The apparatus according to claim 12, the electrical activity comprising local activation time values.

14. The apparatus according to claim 13, the processor being configured to present the region of the map by the focus of the arrhythmia comprises plotting the local activation time values against their respective locations.

15. The apparatus according to claim 12, the arrhythmia comprising a rotor having at least one focus.

16. The apparatus according to claim 12, the arrhythmia comprising a focal.

17. The apparatus according to claim 12, the processor being configured to present the region of the map comprising the geometric center by presenting, in the circle, an icon at a position corresponding to a location of the focus of the arrhythmia relative to the geometric center.

18. The apparatus according to claim 12, the processor being configured to present the circle and the region of the map by overlaying the circle on the electroanatomical map.

19. The apparatus according to claim 12, the processor being further configured to present, within the circle, a path of the arrhythmia from the focus of the arrhythmia.

20. The apparatus according to claim 12, the intracardiac catheter comprising a balloon catheter.

21. The apparatus according to claim 12, the intracardiac catheter comprising a basket catheter.

22. The apparatus according to claim 12, the processor being configured to generate the electroanatomical map by presenting the map on the display at a first resolution, and the processor being configured to present the region by presenting the region at a second resolution greater than the first resolution.

23. A computer software product, operated in conjunction with an intracardiac catheter having a distal end comprising a plurality of electrodes, the product comprising a non-transitory computer-readable medium, in which program instructions are stored, which instructions, when read by a computer, cause the computer:

(a) to receive, from the intracardiac catheter positioned within a heart of a subject, first signals from at least three of the electrodes responsive to electrical activity in myocardial tissue with which the at least three of the electrodes are in contact;

(b) to receive, from at least one of the intracardiac catheter or at least one body surface electrode applied to a body surface of the subject, second signals that are indicative of respective location coordinates of the at least three electrodes within the heart;

(c) to process the second signals so as to compute the respective location coordinates of the at least three electrodes and to determine a geometric center of the respective location coordinates;

(d) to generate, based on the first signals and the second signals, an electroanatomical map for an area of the myocardial tissue comprising the determined geometric center;

(e) to determine, in the map, a focus of an arrhythmia in the area of the myocardial tissue;

(f) to present, on a display, a circle; and (g) to present, within the circle, a region of the map comprising the geometric center and the focus of the arrhythmia so that the geometric center on the map aligns with a center of the circle, the region of the map presented within the circle indicating a spatial relationship between the geometric center and the focus of the arrhythmia.

* * * * *